US00PP32721P2

(12) United States Plant Patent
Clarkson

(10) Patent No.: US PP32,721 P2
(45) Date of Patent: Jan. 5, 2021

(54) ***RUBUS* PLANT NAMED 'BWPRASP01'**

(50) Latin Name: ***Rubus idaeus* hybrid**
Varietal Denomination: BWPRASP01

(71) Applicant: Berryworld Plus Limited, Broxbourne (GB)

(72) Inventor: Graham John Joseph Clarkson, Faversham (GB)

(73) Assignee: BERRYWORLD PLUS LIMITED, Broxbourne (GB)

( * ) Notice: Subject to any disclaimer, the term of this patent is extended or adjusted under 35 U.S.C. 154(b) by 0 days.

(21) Appl. No.: 16/873,509

(22) Filed: Apr. 24, 2020

(30) Foreign Application Priority Data

Jul. 30, 2019 (QZ) ..... PBR 2019/1866

(51) Int. Cl.
*A01H 5/08* (2018.01)
*A01H 6/74* (2018.01)

(52) U.S. Cl.
USPC ..... Plt./204
CPC ..... *A01H 6/7499* (2018.05)

(58) Field of Classification Search
USPC ..... Plt./204
CPC ..... A01H 5/08
See application file for complete search history.

*Primary Examiner* — Kent L Bell
(74) *Attorney, Agent, or Firm* — Penny J. Aguirre

(57) ABSTRACT

A new cultivar of *Rubus idaeus* hybrid plant named 'BWPRASP01' that is characterized by its fruit production on primocanes, its consistently large fruit that are light red in color, its consistent fruit quality throughout the cropping season, its extended shelf life, its easy picking as there is low adherence to the plug and easily accessible through the canopy, its early fruit production, its firm fruit with low acidity, and its versatile cropping schedule as it can be established on different planting dates throughout summer to maintain cropping in autumn and winter in Spain.

2 Drawing Sheets

Botanical classification: *Rubus idaeus* hybrid.
Cultivar designation: 'BWPRASP01'.

CROSS-REFERENCE TO A RELATED APPLICATIONS

This application claims priority to European Community Plant Variety Office (CPVO) Plant Breeder's Rights Application No. 2019/1866 filed Jul. 30, 2019 under 35 U.S.C. 119(f), the entire contents of which is incorporated by reference herein. This application is also related to a Plant Breeder's Rights Application No. filed in Mexico on Jan. 23, 2020, application No. 3100. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of raspberry plant, botanically of hybrid origin with *Rubus idaeus* and other species in its ancestry. 'BWPRASP01' will be referred to hereinafter by its cultivar name, 'BWPRASP01'. 'BWPRASP01' is a new red raspberry plant grown for the fresh fruit market.

'BWPRASP01' arose from an on-going breeding program conducted by the Inventor. 'BWPRASP01' arose from a cross made in spring of 2015 in Faversham, Kent, United Kingdom between unnamed and unpatented proprietary plants in the Inventor's breeding program; designated as accession code F2FH-E5 as the female parent and designated as accession code ECP-E1 as the male parent. The new cultivar was selected in Autumn of 2016 in Cartaya, Huelva, Spain as accession code KAP-E4 from the seedlings that resulted from the above cross.

Asexual propagation of the new cultivar was first accomplished by the Inventor by root cuttings in Faversham, Kent, United Kingdom in spring of 2017. Asexual propagation of the new cultivar by root cuttings, terminal stem cuttings, and tissue culture using meristematic tissue has shown that the characteristics of the new cultivar are stable and reproduced true to type in successive generations.

SUMMARY OF THE INVENTION

The following traits have been repeatedly observed and represent the characteristics of the new cultivar. These attributes in combination distinguish 'BWPRASP01' as a new and unique cultivar of *Rubus*.

1. 'BWPRASP01' exhibits fruit production on primocanes.
2. 'BWPRASP01' exhibits consistently large fruit that are light red in color.
3. 'BWPRASP01' exhibits consistent fruit quality throughout the cropping season.
4. 'BWPRASP01' exhibits an extended shelf life.
5. 'BWPRASP01' exhibits easy picking as there is low adherence to the plug and easily accessible through the canopy.
6. 'BWPRASP01' exhibits early fruit production.
7. 'BWPRASP01' exhibits firm fruit with low acidity.

8. 'BWPRASP01' exhibits a versatile cropping schedule as it can be established on different planting dates throughout summer to maintain cropping in autumn and winter in Spain.

'BWPRASP01' differs from its female parent in producing fruit earlier in the season, in being easier to pick, in having larger fruits that are less juicy, a longer shelf life, and less lateral branches. 'BWPRASP01' differs from its male parent in producing fruit earlier in the season, in being easier to pick, in having larger fruits that are sweeter and juicier with thicker and less glossy skin, and less lateral branches. 'BWPRASP01' can be compared to *Rubus* cultivars 'Diamond Jubilee' (U.S. Plant Pat. No. 25,455) and 'Autumn Glory' (U.S. Plant Pat. No. 25,952)). 'Diamond Jubilee' differs from 'BWPRASP01' in producing fruit later in the season, in having thicker canes with more sparse spines and lower anthocyanin intensity, and fruit that is more round to broad conical in shape with skin that is deeper red in color. 'Autumn Glory' differs from 'BWPRASP01' in producing fruit later in the season, in having slightly thicker canes with lower anthocyanin intensity, and fruit with skin that is dark red in color.

BRIEF DESCRIPTION OF THE DRAWINGS

The accompanying colored photographs illustrate the overall appearance and distinct characteristics of the new *Rubus*. The photographs were taken of plants about 8.5 months in age as grown under high tunnels under natural conditions in 7.5-Liter containers in Cartaya, Huelva, Spain.

The photograph in FIG. 1 provides a view of the fruiting canes of 'BWPRASP01'.

Figure 1:
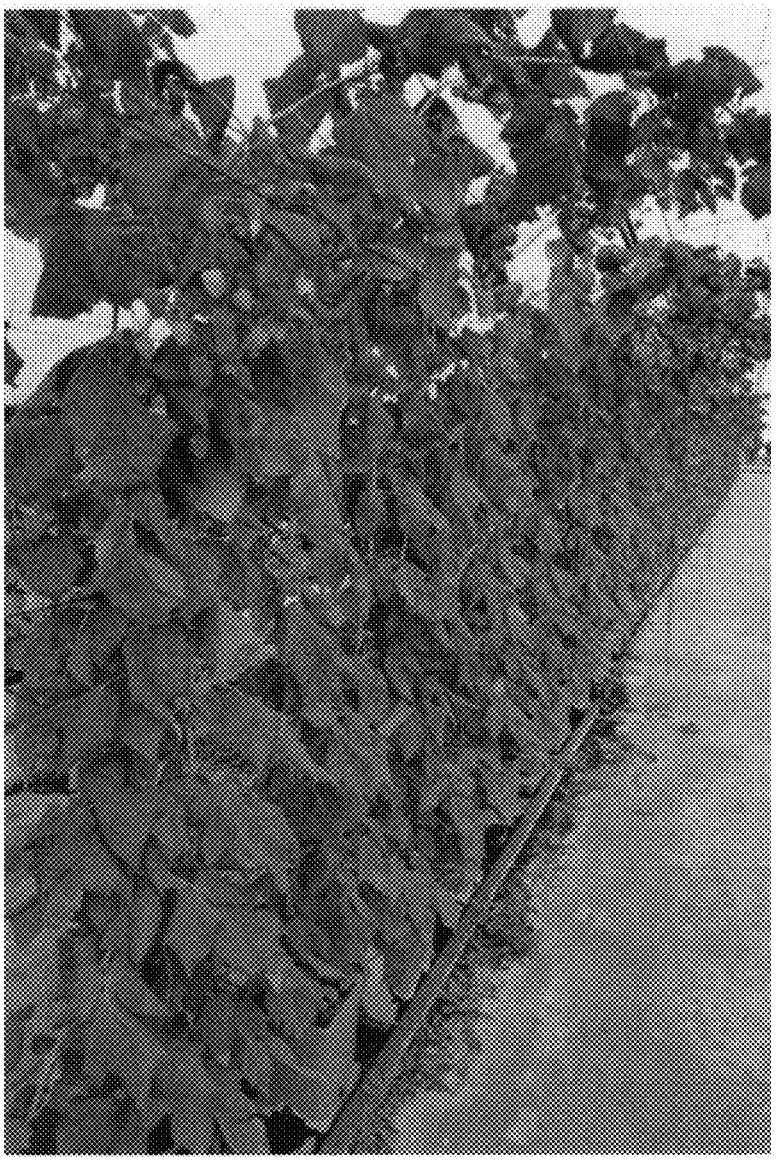
Figure 2:
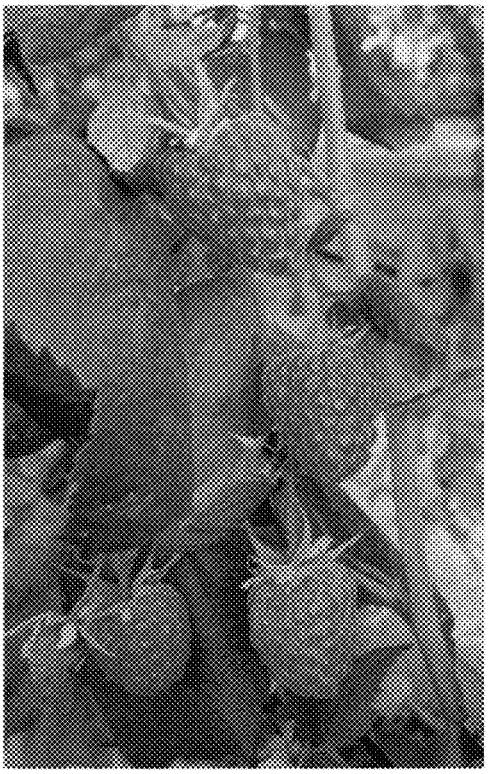

The photograph in FIG. 2 provides a close-up view of the fruit of 'BWPRASP01'.

Figure 3:
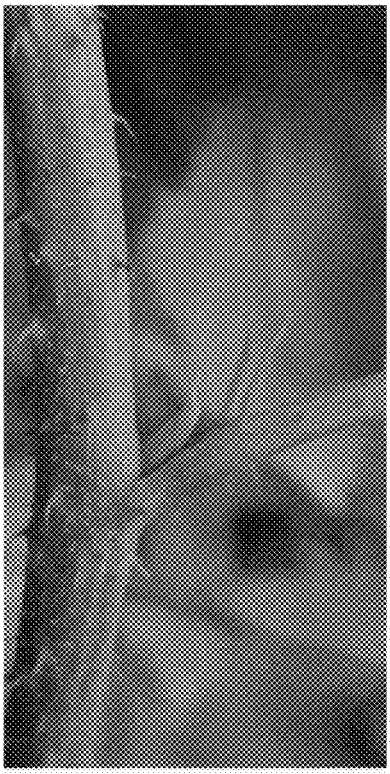

The photograph in FIG. 3 provides a close-up view of a fruiting cane of 'BWPRASP01'.

Figure 4:
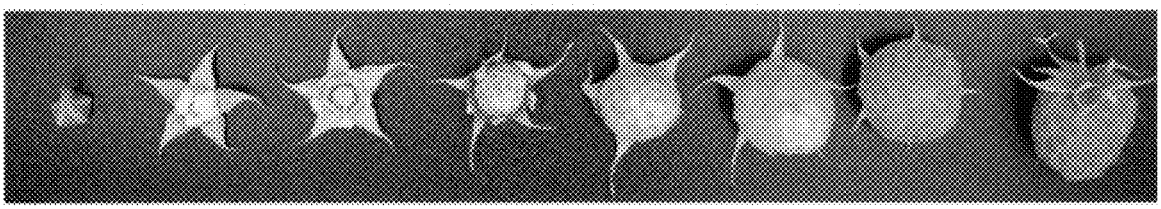

The photograph in FIG. 4 provides a view of the developing flower buds and developing berries of 'BWPRASP01'.

The colors in the photographs are as close as possible with the photographic and printing technology utilized. The colors in the photograph may differ slightly from the color values cited in the detailed botanical description, which accurately describe the colors of the new *Rubus*.

DETAILED BOTANICAL DESCRIPTION OF THE PLANT

The following is a detailed description of plants about 8.5 months in age of the new cultivar as grown under high tunnels under natural conditions in 7.5-Liter containers in Cartaya, Huelva, Spain from rooting cuttings grown in coir in Faversham, Kent, United Kingdom. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—Primocane; September in Cartaya, Spain.

*Plant habit*.—Semi-upright.

*Height and spread*.—Primocanes reach between 1.2 and 1.4 m height at the 10th bud from the tip at the time of fruit production.

*Hardiness*.—At least hardy in U.S.D.A Zones 8 and 10.

*Diseases and pests*.—This variety has not shown any specific susceptibility to pests or diseases except for mild susceptibility to powdery mildew which is well managed by standard crop prophylaxis.

*Root description*.—Fibrous and vigorous.

*Propagation*.—Root cuttings, terminal stem cuttings, and tissue culture.

*Root development*.—Root cuttings fully root in 2 weeks in a coir plug and fully develop in a 7.5-Liter container in about 4 months.

Cane description (primocanes):

*Cane size*.—At 10th bud from tip; 1.2 to 1.4 m in length and 0.57 cm in diameter.

*Cane color*.—144B with anthocyanin 182B.

*Internode length*.—Average of 2.88 cm between the 4th and 10th node.

*Branching habit*.—Moderately branched.

*Fruiting laterals*.—Average of 15.9 cm in length at 10th bud from tip and 11.75 cm in length at 4th bud from tip, 144B with anthocyanin 182B, surface glabrous with spines dense to very dense; 4.87 per square cm at 10th bud, conical in shape with very thin tips that hooks downward, sturdy, average of 2.28 mm in length, 182B in color, no glaucosity observed on full grown shoots, young shoots minimal and 145A in color with anthocyanin present 182B.

Foliage description:

*Leaf shape*.—Ovate in overall form.

*Leaf division*.—Compound; 3 leaflets.

*Leaf attachment*.—Petiolate.

*Leaf orientation*.—Flat to pendant.

*Leaf size*.—An average of 17.8 cm in length and 17.7 cm in width; 1:1 ratio.

*Leaflet shape*.—Broad ovate.

*Leaflet base*.—Cordate.

*Leaflet apex*.—Acuminate.

*Leaflet venation*.—Palmate, color primarily matches leaf color.

*Leaflet margins*.—Doubly serrate, un-lobed, low to moderate undulation.

*Relative position of lateral leaflet*.—Non-overlapping.

*Profile of leaflet cross-section*.—Convex.

*Leaflet arrangement*.—One terminal and 1 to 2 lateral pairs.

*Leaflet attachment*.—Stalked.

*Leaflet surface*.—Glabrous with moderate rugosity.

*Leaflet color*.—Upper surface NN137B, lower surface 191C.

*Leaflet size*.—Terminal; an average of 11.43 cm in length and 7.12 cm in width (ratio 1.6), lateral; an average of 8.72 cm in length and 5.41 cm in width (ratio 1.6).

*Petioles*.—Round in shape, an average of 4.5 cm in length and 2.28 mm in width. color upper surface 144B, color lower surface 145C.

*Stipules*.—2 per petiole, held erect, slightly pubescent but mainly smooth, an average of 9 mm in length and 0.5 mm in width, lanceolate in shape, color 144D.

*Rachis*.—Round in shape, an average of 1.85 cm in length and 1.4 mm in width.

Inflorescence description:

*Inflorescence*.—Raceme.

*Pedicels*.—Oval in shape, an average of 2.85 mm in length and 1.22 mm in width, color 146C, surface glabrous with spines and prickles.

*Flower type*.—Spreading calyx with a center of a ring of numerous upright stamens and with numerous pistils in the center, petals are quickly shed upon opening.

*Flower fragrance*.—None.

*Flower size*.—3.36 cm in diameter.

*Sepals*.—Five, base truncate, apex acuminate, both surface downy.

*Petals*.—Five, dropped at fruit maturity, an average of 9.9 mm in length and 4.16 mm in width, ovate in shape with a rounded apex and oblong base, glabrous on upper and lower surfaces, thin, color NN155C.

*Fertility*.—Self-compatible.

Fruit description:

*Fruit size*.—Average of 2.68 cm in length and 2.55 cm in width, ratio 1.05.

*Fruit color*.—Immature; 145B, early maturing;160C, maturing; 35B, ripe; 42B.

*Fruit shape*.—The aggregate fruit is conical.

*Fruit adherence to plug*.—Low.

*Drupelets*.—An average of 76.2 drupelets per aggregate fruit which are globose in shape and firm, large, surface is moderately glossy, style and stigma; persistent at maturity.

*Persistence of bracts*.—Persistent.

*Receptacle*.—Conical to blunt conical in shape and, persistent on the plant at harvest, fleshy, size varies with individual fruit size.

*Fruit maturity date*.—Early producing; typically October 3rd in Cartaya, Spain.

*Seed*.—Kidney shaped, 1 per drupelet.

*Cropping frequency*.—Produced on same year cane (primocanes), versatile cropping schedule as it can be established on different planting dates throughout summer to maintain cropping in autumn and winter in Spain.

*Flavor*.—Sweet.

*Brix*.—10.6° under conditions grown.

*Yield*.—559 g/cane in Spain measured throughout the harvest season October to December.

*Fruit weight*.—Typically 6.43 g in the United Kingdom.

*Market use*.—Fresh fruit, commercial production.

*Shelf life*.—Extended, fruits can be transported and kept in chilled conditions without noticeable deterioration for 7 or more days after picking.

It is claimed:

1. A new and distinct cultivar of *Rubus idaeus* hybrid plant named 'BWPRASP01' as herein illustrated and described.

* * * * *